United States Patent [19]

Blackburn et al.

[11] 3,960,870

[45] June 1, 1976

[54] ALKANESULFONIC ACID SALTS OF DECININE

[75] Inventors: Dale W. Blackburn, Moorestown, N.J.; Henry Cecil Caldwell, Ambler, Pa.

[73] Assignee: SmithKline Corporation, Philadelphia, Pa.

[22] Filed: Aug. 2, 1974

[21] Appl. No.: 494,142

Related U.S. Application Data

[63] Continuation-in-part of Ser. No. 351,702, April 16, 1973, abandoned.

[52] U.S. Cl............................ 260/293.53; 424/267
[51] Int. Cl.$^2$....................................... C07D 221/18
[58] Field of Search............................... 260/293.53

[56] References Cited
UNITED STATES PATENTS

| | | | |
|---|---|---|---|
| 3,541,066 | 11/1970 | Wolf.................................. | 260/288 |
| 3,741,972 | 6/1973 | Bonati............................ | 260/293.53 |
| 3,763,168 | 10/1973 | Carabateas..................... | 260/293.53 |

OTHER PUBLICATIONS

Ferris et al., J. Am. Chem. Soc. 93, 2958–2962 (1971).
Cram et al., "Organic Chemistry," 2nd Ed., McGraw–Hill, New York, (1964), pp. 184–185.

*Primary Examiner*—G. Thomas Todd
*Attorney, Agent, or Firm*—Joan S. Keps; Richard D. Foggio; William H. Edgerton

[57] ABSTRACT

The compounds are alkanesulfonic acid salts of decinine. These salts are water soluble. Decinine and the salts thereof have glucocorticoid-like water diuretic and anti-inflammatory activity.

4 Claims, No Drawings

ALKANESULFONIC ACID SALTS OF DECININE

This application is a continuation-in-part of Ser. No. 351,702, filed Apr. 16, 1973, now abandoned.

This invention relates to new water soluble salts of decinine. These salts are alkanesulfonates which are formed with 1 mole of decinine and 1 mole of the alkanesulfonic acid or 2 moles of decinine and 1 mole of the alkanedisulfonic acid.

The alkanesulfonate salts of decinine which are the compounds of this invention are represented herein by the following formula:

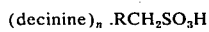

(decinine)$_n$ .RCH$_2$SO$_3$H in which:

$n$ is 1 and R is H or CH$_3$ or
$n$ is 2 and R is SO$_3$H or CH$_2$SO$_3$H.

Preferably, in the above formula, $n$ is 2 and R is CH$_2$SO$_3$H, that is the preferred compound of this invention is decinine 1,2-ethanedisulfonate (2:1) salt.

Decinine is a Lythraceae alkaloid which has been isolated from *Decodon verticillatus* (Ferris, *J. Org. Chem.* 27:2985, 1962) and *Lagerstroemia indica* (Ferris et al., *J. Am. Chem. Soc.* 93:2958, 1971). Decinine is represented by the following structural formula:

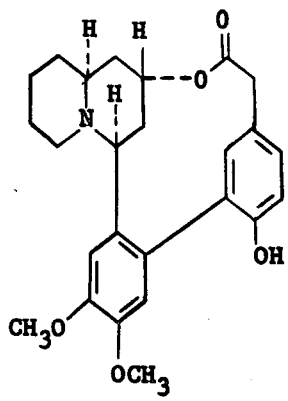

It has been found that, although decinine is not steroidal in chemical structure, is possesses the useful properties of the glucocorticoids; in particular, decinine reduces tissue barrier permeabilities in an animal organism and has glucocorticoid-like water diuretic and anti-inflammatory activity.

Water diuretic activity shows that a substantial effect on tissue barrier permeabilities acting to restore resistance to free diffusion is produced. Drugs having this activity may be expected to restore normal permeabilities to a variety of tissues and therefore possess many diverse pharmacological utilities. The action on cell permeabilities is an effect on one of the basic requirements of all cells in the maintenance of their structure and function.

Decinine is more effective and differs from glucocorticoids, for example prednisone, in completely antagonizing the antidiuretic properties of antidiuretic hormone (ADH) while glucocorticoids only partially antagonize ADH. As a completely effective antagonist of ADH, decinine may possess hypotensive and coronary vasodilator activity.

A water diuretic should be a desirable adjunctive therapy in treatment of obesity to mobilize fluids as fats are catabolized.

Since many reports indicate a retention of water during the depressive phase of manic-depressive psychoses, a water diuretic may have a desirable antidepressant activity. Glucocorticoids have been reported to involve some degree of euphoria but have many side-effects.

Decinine can be used therapeutically in edematous conditions, particularly where hyponatremia exists, for example in congestive heart failure and cirrhosis of the liver and also can be used therapeutically, as glucocorticoids are, in treatment of nephrosis.

The water diuretic activity of decinine is demonstrated in adrenalectomized (ADX) water-loaded rats at doses of about 5 mg./kg. to about 60 mg./kg. orally. The ability to remedy defective water excretion by ADX rats, determined by this test, is a means of determining glucocorticoid-like activity. Wiebelhaus et al., *Third International Congress of Nephrology*, Vol. II, page 296, Washington, D.C., 1966.

Water diuretic activity of decinine is also demonstrated by its ability to antagonize the effects of antidiuretic hormone (ADH), i.e. vasopressin, in water-loaded rats. This anti-ADH activity is shown by administering antidiuretic hormone to control animals and to animals treated with decinine, and measuring urine volumes. Decinine produces anti-ADH activity at doses of about 1 mg./kg. to about 30 mg./kg. orally, with maximal activity at doses of about 10 mg./kg. to about 30 mg./kg. orally.

The anti-inflammatory activity of decinine is shown by its ability to inhibit carrageenin-induced abcess in rats at doses of about 5 mg./kg. to about 100 mg./kg. orally and to inhibit rat paw edema at doses of about 5 mg./kg. to about 45 mg./kg. orally.

Also, decinine inhibits adjuvant-induced polyarthritis in rats as shown by decrease in the inflamed hind leg volumes in experimental rats, when compared to controls, produced by oral administration of decinine.

The procedures for determining water diuretic activity in adrenalectomized water-loaded rats and anti-inflammatory activity by carrageenin-induced abcess and rat paw edema tests are described by Maass et al., *J. Pharm. Exp. Therap.* 163:239–249 (1968).

Decinine is soluble in water only to the extent of about 0.07 mg./ml. The hydrochloride, bisulfate, phosphate and mono-tartrate salts are no more water soluble, and in some cases are less water soluble, than decinine as the base. The new alkanesulfonic acid salts of decinine are much more water soluble. In particular, decinine 1,2-ethanedisulfonate (2:1) salt, which is the preferred salt of this invention, is soluble to the extent of about 1000 mg./ml. of water.

The alkanesulfonate salts of this invention are prepared by reacting decinine with an alkanesulfonic acid in approximately equal molar amounts in aqueous miscible solvent such as ethanol, preferably at elevated temperature, with isolation of the salt by cooling. The salts may also be prepared in aqueous immiscible solvent such as ethyl ether or chloroform with the salt separating directly. The salts may also be prepared by the classical method of double decomposition of appropriate salts which is well known to the art.

The alkanesulfonate salts of this invention have the pharmacological activity described hereinabove for decinine.

The water soluble salts of this invention are advantageous for preparing liquid pharmaceutical formulations for oral and injectable use and also for preparing quickly dissolving solid pharmaceutical formulations.

The following examples are not limiting but are illustrative of this invention.

EXAMPLE 1

1,2-Ethanedisulfonic acid dihydrate (11.30 g.) is dissolved in 100 ml. of absolute ethanol and 44 ml. of the solution is added rapidly with stirring to 8.760 g. of decinine in 90 ml. of boiling absolute ethanol. The mixture is allowed to stand for 3 hours at room temperature. The precipitate is filtered off, washed with absolute ethanol and then with petroleum ether and then dried in vacuo at 75°C. to give the ethanolate of decinine 1,2-ethanedisulfonate (2:1) salt. This ethanolate is dried in vacuo at 120°–125°C. to give decinine 1,2-ethanedisulfonate (2:1) salt.

EXAMPLE 2

Decinine (1.1 g.) is dissolved in 12 ml. of boiling absolute ethanol. To this solution is added 0.24 g. of methanesulfonic acid in 3 ml. of absolute ethanol. The mixture is cooled and the precipitate is filtered, washed with absolute ethanol, then with petroleum ether and dried in vacuo at 72°C. to give decinine methanesulfonate.

EXAMPLE 3

Decinine (1.1 g.) is dissolved in 12 ml. of boiling absolute ethanol. To this solution is added 0.88 g. of 50% aqueous methanedisulfonic acid in 3 ml. of absolute ethanol. The solution is heated at reflux for 15 minutes, then cooled and filtered. The solid material is washed with absolute ethanol, then with petroleum ether and dried in vacuo to give decinine methanedisulfonate (2:1) salt.

EXAMPLE 4

By the procedure of Example 1 using ethanesulfonic acid, decinine ethanesulfonate is prepared.

What is claimed is:

1. An alkanesulfonate salt of decinine of the formula:

$$(decinine)_n \cdot RCH_2SO_3H$$

in which:

$n$ is 1 and R is H or $CH_3$ or $n$ is 2 and R is $SO_3H$ or $CH_2SO_3H$.

2. The alkanesulfonate salt of claim 1 in which $n$ is 2 and R is $CH_3SO_3H$.

3. The alkanesulfonate salt of claim 1 in which $n$ is 1 and R is H.

4. The alkanesulfonate salt of claim 1 in which $n$ is 2 and R is $SO_3H$.

* * * * *